(12) United States Patent
Demirev et al.

(10) Patent No.: US 9,353,396 B2
(45) Date of Patent: *May 31, 2016

(54) SYSTEM FOR DETERMINING DRUG RESISTANCE IN MICROORGANISMS

(71) Applicant: The Johns Hopkins University, Baltimore, MD (US)

(72) Inventors: Plamen A. Demirev, Ellicott City, MD (US); Nathan A. Hagan, Ellicott City, MD (US); Miquel D. Antoine, Columbia, MD (US); Jefffrey S. Lin, Silver Spring, MD (US); Andrew B. Feldman, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 409 days.

This patent is subject to a terminal disclaimer.

(21) Appl. No.: 13/924,749

(22) Filed: Jun. 24, 2013

(65) Prior Publication Data
US 2013/0288356 A1    Oct. 31, 2013

Related U.S. Application Data

(62) Division of application No. 13/029,830, filed on Feb. 17, 2011, now Pat. No. 8,481,281.

(60) Provisional application No. 61/350,705, filed on Jun. 2, 2010.

(51) Int. Cl.
| G01N 24/00 | (2006.01) |
| C12Q 1/02 | (2006.01) |
| C12Q 1/18 | (2006.01) |

(52) U.S. Cl.
CPC . *C12Q 1/025* (2013.01); *C12Q 1/18* (2013.01)

(58) Field of Classification Search
CPC .... C07K 1/13; C12Q 2565/627; C12Q 1/025; C12Q 1/18; C12Q 1/04; C12P 21/00; C12P 21/005; G01N 2800/52; G01N 33/6848; G01N 33/6803; G01N 33/6851; G01N 30/7266; B01J 2219/00725; B01J 2219/00581
See application file for complete search history.

(56) References Cited

U.S. PATENT DOCUMENTS

| 6,379,920 B1 | 4/2002 | El-Sayed et al. |
| 6,642,059 B2 | 11/2003 | Chait et al. |

(Continued)

FOREIGN PATENT DOCUMENTS

| DE | 10038694 | 9/2003 |
| EP | 0457789 | 11/1992 |

(Continued)

OTHER PUBLICATIONS

Oeljeklaus et al., "Mass Spectrometry-Driven Approaches to Quantitative Proteomics and Beyond" ("Comprehensive Analytical Chemistry. Protein Mass Spectrometry", v. 52, ed. Whitelegge, 2009, pp. 411-448; only pp. 413, 414 and 417 are provided.*

(Continued)

*Primary Examiner* — Yelena G Gakh
(74) *Attorney, Agent, or Firm* — Noah J. Hayward

(57) ABSTRACT

The present invention is based on the discovery that drug resistance in microorganisms can be rapidly and accurately determined using mass spectrometry. A mass spectrum of an intact microorganism or one or more isolated biomarkers from the microorganism grown in drug containing, isotopically-labeled media is compared with a mass spectrum of the intact microorganism or one or more isolated biomarkers from the microorganism grown in non-labeled media without the drug present. Drug resistance is determined by predicting and detecting a characteristic mass shift of one or more biomarkers using algorithms. The characteristic mass shift is indicative that the microorganism is growing in the presence of the drug and incorporating the isotopic label into the one or more biomarkers, resulting in change in mass.

9 Claims, 5 Drawing Sheets

(56) References Cited

U.S. PATENT DOCUMENTS

| | | |
|---|---|---|
| 7,635,573 B2 | 12/2009 | Fischer |
| 2006/0029574 A1 | 2/2006 | Albitar et al. |
| 2008/0009029 A1 | 1/2008 | Govorun et al. |

FOREIGN PATENT DOCUMENTS

| | | |
|---|---|---|
| GB | 2438066 | 11/2007 |
| WO | 03102022 | 12/2003 |

OTHER PUBLICATIONS

Fernando J. Pineda et al., Testing the Significance of microorganism Identification by Mass Spectrometry and Proteome Database Search; Analytical Chemistry, vol. 72, No. 16, Aug. 15, 2000, pp. 3739-3744.

Plamen A. Demi Rev et al., Bioinformatics and Mass spectrometry for Microorganism Identification: Proteome-Wide 2 Post-Translational Modifications and Database Search Algorithms for Characterization of Intact H. pylori; American D Chemical Society, vol. 73, No. 19, Oct. 1, 2001, pp. 4566-4573.

Plamen A. Demi Rev et al., Tandem Mass Spectrometry of Intact proteins for Characterization of Biomarkers from Bacillus cereus T Spores; Analytical Chemistry, vol. 73, No. 23, Dec. 1, 2001, pp. 5725-5731.

Plamen A. Demirev et al., Top-Down Proteomics from Rapid Identification of Intact Microorganisms; Analytical Chemistry, vol. 77, No. 22, Nov. 15, 2005, pp. 7455-7461.

Plamen A. Demi Rev et al., On-Line supporting information, Top-down proteomics for rapid identification of intact microorganisms; pp. 1-6.

Plamen A. Demi Rev et al., Microorganism Identification by Mass Spectrometry and Protein Database Searches, Analytic Chemistry, vol. 71, No. 14, Jul. 15, 2999, pp. 2732-2738.

Plamen A. Demi Rev et al., Mass Spectrometry for Rapid Characterization of Microorganisms, Annu. Rev. Anal. Chem. 2008, 1:71-93.

Plamen A. Demi Rev et al., Bioinformatics-Based Strategies for Rapid Microorganism Identification by Mass Spectrometry; Johns Hopkins APL Technical Digest, vol. 25, No. 1 (2004), pp. 27-37.

Nathan A. Hagan et al., MALDI mass spectrometry for rapid detection and characterization of biological threats, 9 Appreared in: Rapid Characterization of Microorganisms by Mass Spectrometry (ed.C. Fenselau & P. Demirev), ACS Symposium Series Vol., Washington DC 2011, pp. 1-19.

Nico Jehmlich et al., Protein-based stable isotope probing (Protein-SIP) reveals active species within anoxic mixed cultures; The ISME Journal (2008) 2, pp. 1122-1133.

Roman A. Zubarev et al., Isotope Depletion of Large Biomolecules: Implications for Molecular Mass Measurements; 1998 Almerican Society for Mass Spectrometry. Published by Elsevier Science Inc., pp. 150-156.

Plamen A. Demi Rev et al., Mass spectrometry in biodefense; Journal of mass Spectrometry 2008, pp. 1441-1457.

Matihew Meselson et al., The Replication of DNA in *Escherichio coli;* Biology: Meselson and Stahl, vol. 44, 1958, pp. 671-682.

\* cited by examiner

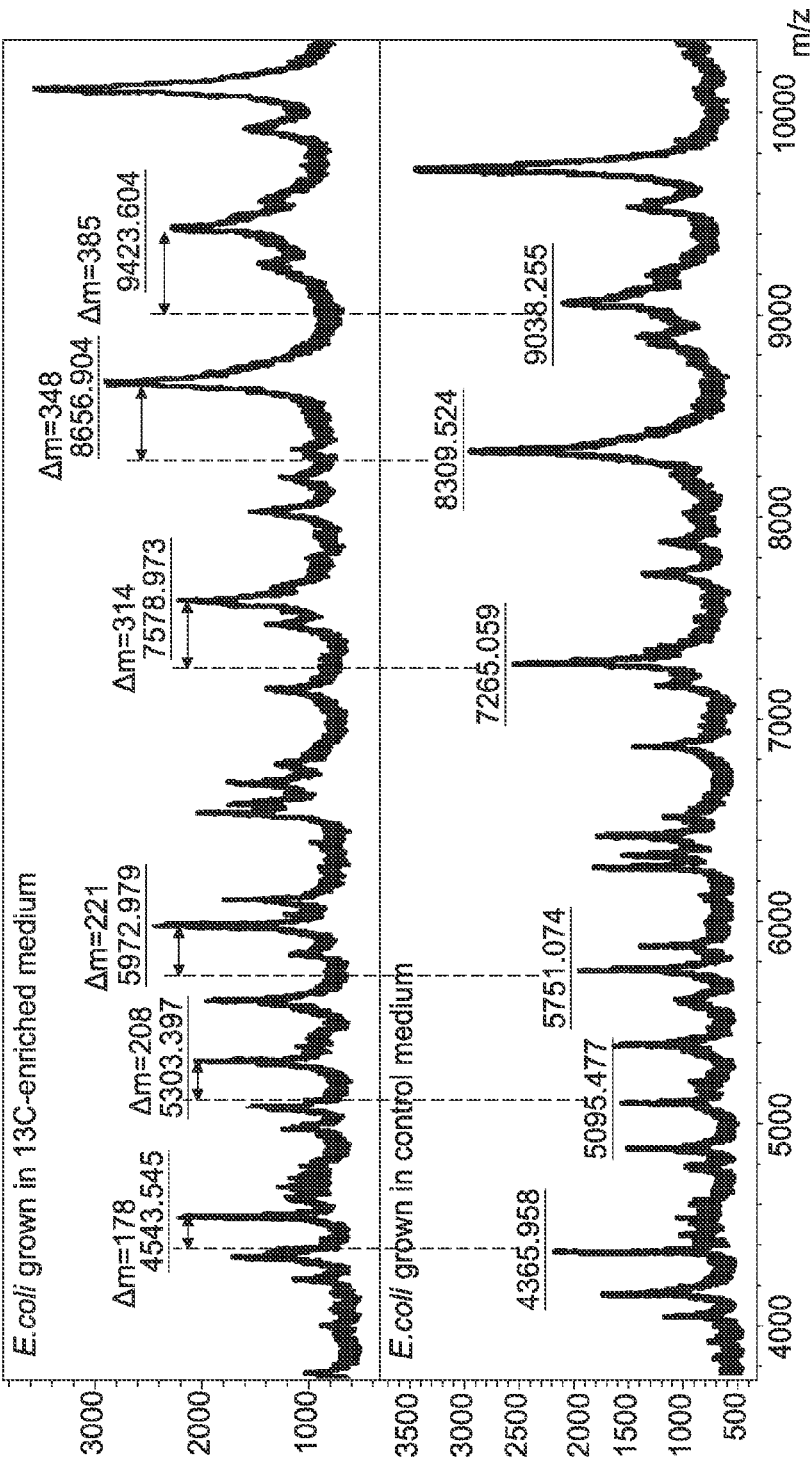

SYSTEM FOR DETERMINING DRUG RESISTANCE IN MICROORGANISMS

CROSS REFERENCE TO RELATED APPLICATIONS

This application is a divisional of prior-filed, co-pending U.S. application Ser. No. 13/029,830, filed Feb. 17, 2011, which claims priority to and the benefit of prior-filed U.S. Provisional Application No. 61/350,705, filed Jun. 2, 2010, the contents of each of which are herein incorporated by reference in their entireties.

BACKGROUND

The field of the disclosure relates to microbiology. In particular, the field relates to detection of drug resistance in microorganisms. The field also relates to biochemical analysis by mass spectrometry.

Bioinformatics derives knowledge from computer analysis of biological data. This can consist of the information stored in the genetic code, but also experimental results from various sources, patient statistics, and scientific literature. Research in bioinformatics includes method development for storage, retrieval, and analysis of the data. Bioinformatics is a rapidly developing branch of biology and is highly interdisciplinary, using techniques and concepts from informatics, statistics, mathematics, chemistry, biochemistry, physics, and linguistics. It has many practical applications in different areas of biology and medicine.

It is well documented that the evolution of drug-resistant organisms are on the rise, and may lead to "superbugs," untreatable by currently-available pharmaceuticals. This poses an extremely serious world-wide public health problem. Therefore, rapid and accurate determination of the resistance of a particular microorganism to the effects of different antibiotics is very important, with applications in a number of fields—from clinical microbiology and diagnostics of infectious diseases to the timely responses in case of a bioterrorism attack.

A number of classical microbiology techniques have been used to determine drug resistance. These techniques include monitoring organism proliferation in the presence of the drug, and the resulting biosynthesis of organism-specific molecules (DNA, proteins, etc.). For example, a change in optical density (turbidity) of culture suspensions is an indication of growth. These techniques typically take between 24 and 48 hours.

Recently, somewhat faster molecular level methods have been applied. Real-time quantitative PCR has been used to monitor the quantity of DNA in various gram-positive and gram-negative species in an effort to create an antibiotic susceptibility assay (J. Rolain, M. Mallet, P. Fournier, D. Raoult, and *J. Antimicrob. Chemother.* 54 (2004) 538-541, "Real-time PCR for universal antibiotic susceptibility testing."). However, such PCR methods typically are by default "narrow-band," i.e., they are generally used only after an organism has been identified in the sample.

In addition, techniques have been developed for labeling and characterizing biomolecules. Isotopes are atoms of the same element that have different masses. The isotopes of a particular element all have the same number of protons and electrons, but different number of neutrons. Isotopes provide a useful tool to scientists because although they have different masses, they do not differ significantly in their chemical behavior. Isotopic labeling is the technique used to label and track drugs or molecules that incorporate defined isotopes.

Further, isotopic labeling has been employed with various drugs and biomolecules to study their structures, functions and in vivo processing or production. Isotopic labeling of drugs or biomolecules allows for an easy and effective way to study changes in biomolecules or drugs without impacting their functions.

Many of the existing systems and methods for determining drug resistance in microbes are neither rapid nor accurate. For instance, it is often necessary to wait a number of hours or days for microbes to go through various growth stages in order to characterize them. This is particularly problematic in both infectious disease and bioterrorism scenarios where time is of the essence in identifying, treating, or eradicating certain virulent and unknown pathogens. In addition, many existing tests and systems often produce false positives in identifying the existence or presence of various microbes. False identifications can lead to false diagnosis or further contaminations due to lack of containment or treatment.

For these reasons, what are needed are systems and methods for rapidly detecting, identifying, and characterizing drug-resistant and pathogenic microorganisms. Also needed are systems and methods that can accurately determine the presence or existence of such microbes. Further needed are systems and methods that are highly reliable and effective for providing accurate identifications and characterizations of drug-resistant and pathogenic microbes.

SUMMARY

Accordingly, one aspect of the present invention is to provide accurate and predictable systems and methods for detecting drug resistance in microorganisms using mass spectrometry.

Another aspect of the present invention is to provide algorithms that together with mass spectrometry more accurately predict and confirm drug resistance in microorganisms using mass spectrometry.

Various of these and other aspects are provided for in certain embodiments of the present invention.

In one aspect, the invention provides a system for determining the resistance of a microorganism to a drug, comprising: (a) a sample growth and processing module for isotopic labeling and processing of a sample; (b) a mass spectrometry acquisition module down-stream from the sample growth and processing module for detecting and analyzing the isotopically-labeled and processed sample; and (c) an algorithmic module down-stream from the mass spectrometry acquisition module for processing the results from (b) and determining whether the microorganism is drug-resistant.

In another aspect, the invention provides a method for determining the resistance of a microorganism to a drug by detecting growth of the microorganism in the presence of the drug, comprising: (a) incubating the microorganism in i) an isotopically-labeled growth medium comprising at least one drug and an isotopic label, wherein the microorganism incorporates the isotopic label into one or more biomarker molecules of the microorganism during growth in the medium; and ii) a control growth medium that lacks the drug and the isotopic label, wherein the one or more biomarker molecules of the microorganism remain unlabeled during growth in the medium; (b) applying the microorganism biomarker molecules of (a) to a mass spectrometry system to produce ion mass fragments of the biomarker molecules; (c) predicting a mass shift of the one or more unlabeled biomarker molecules of (a)(ii) using a first algorithmic analysis based on incorporation of the isotopic label of (a)(i); and (d) comparing the predicted mass shift of (c) with an observed mass of the one or more biomarker molecules of the microorganism growing in the isotopically-labeled medium with drug of (a)(i) using a second algorithmic analysis, based on which a probability can be determined that the biomarker molecules in the two media match, thereby determining the resistance of the microorganism to the drug.

It is to be understood that both the foregoing general description of aspects of the invention and the following detailed description are exemplary, and thus do not restrict the scope of the invention.

BRIEF DESCRIPTION OF THE DRAWINGS

The skilled artisan will understand that the drawings, described below, are for illustration purposes only. The drawings are not intended to limit the scope of the present teachings in any way.

FIG. 2 (A) is an embodiment depicting a sample growth and processing module.

FIG. 3 shows mass spectrometry results using MALDI TOF MS of intact *E. coli* microorganisms grown in $^{13}$C isotopically enriched medium compared to *E. coli* grown in control medium. (A) shows *E. coli* grown in $^{13}$C-enriched medium while (B) shows *E. coli* grown in control medium having natural carbon isotopic abundance.

DETAILED DESCRIPTION

Figure 1:
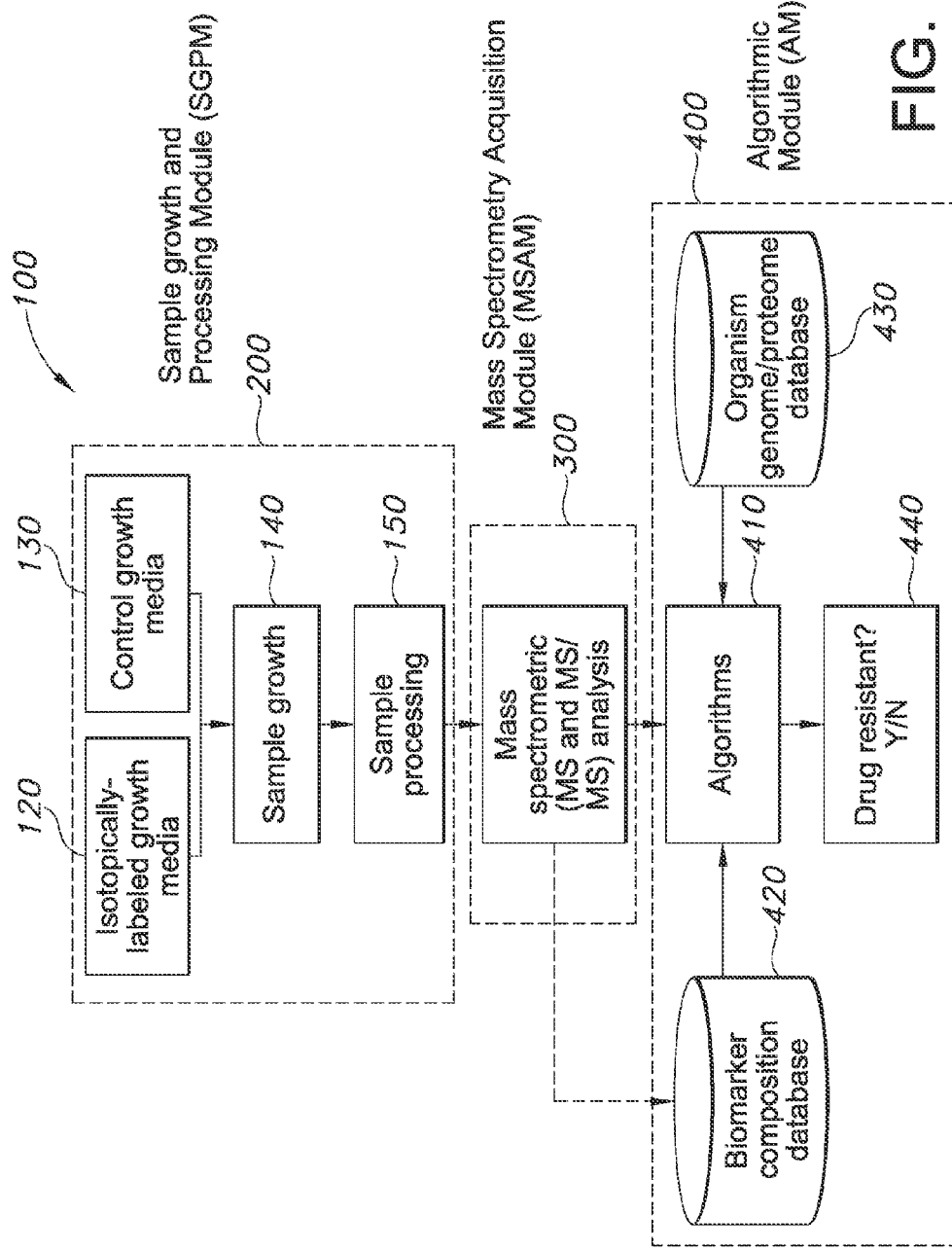
FIG. 1 shows a schematic diagram of an embodiment of the mass spectrometry-based system according to one example embodiment of the present invention to establish drug resistance/susceptibility of microorganisms.

Effective responses to bioterrorism, infectious diseases, or drug-resistant bacteria, all require rapid and accurate microorganism identification. Example embodiments of the present invention is based on the surprising discovery that drug resistance in microorganisms can be rapidly and accurately determined using mass spectrometry. In accordance with the embodiments as described herein, a mass spectrum of an intact microorganism or one or more isolated biomarkers from the microorganism grown in drug containing, isotopically-labeled media is compared with a mass spectrum of the intact microorganism or one or more isolated biomarkers from the microorganism grown in non-labeled media without the drug present. Drug resistance is determined by detecting a characteristic mass shift of one or more biomarkers using algorithms. The characteristic mass shift is indicative that the microorganism is growing in the presence of the drug and incorporating the isotopic label into the one or more biomarkers, resulting in a change in mass.

Unless otherwise noted, technical terms are used according to conventional usage. Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar technical references.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the terms "antimicrobial," "drug" and "antibiotic" are used interchangeably. The terms antimicrobial, drug or antibiotic describe a substance that can kill or inhibit the growth of microorganisms.

As used herein, a microorganism that is "resistant" to a drug is a microorganism that is capable of growth in the presence of the drug. In some cases, the resistance to the drug is total or complete, in that growth is not inhibited compared with growth in the absence of the drug. In some cases, resistance is partial, insofar as growth in the presence of the drug is modestly inhibited or attenuated as compared with growth in the absence of the drug.

In one embodiment, the invention provides a system for determining the resistance of a microorganism to a drug, comprising: (a) a sample growth and processing module for isotopic labeling and processing of a sample; (b) a mass spectrometry acquisition module down-stream from the sample growth and processing module for detecting and analyzing the isotopically-labeled and processed sample; and (c) an algorithmic module down-stream from the mass spectrometry acquisition module for processing the results from (b) and determining whether the microorganism is drug-resistant.

FIG. 1 shows an embodiment of a system 100 for determining drug resistance in a microorganism. The system 100 comprises a sample growth and processing module (SGPM) 200, a mass spectroscopy acquisition module (MSAM) 300 and an algorithmic module (AM) 400. In one embodiment of the system, the algorithmic module 400 is downstream from the mass spectroscopy acquisition module 300; and the mass spectroscopy acquisition module 300 is downstream from the sample growth and processing module 200. Other embodiments and organization of the system can be possible.

In some embodiments, the sample growth and processing module (SGPM) comprises an isotopically-labeled growth media 120, a control growth media 130, parameters for sample growth 140, and sample processing 150. In some embodiments, culture media are solutions containing all of the nutrients and necessary physical growth parameters necessary for microbial growth or other media as described herein.

Further, the isotopically-labeled growth media comprises an isotope that is capable of being incorporated into one or more biomarker molecules produced from the growth of a microorganism that is placed in the media. The isotopic labeled growth media 120 can optionally comprise a drug or other similar type component to test for drug resistance.

In some embodiments, the control growth media 130 comprises all the necessary media for growing a microorganism of interest or other media as described herein. The media can comprise media with natural isotopic abundance. In other words, no enriched isotope as employed in the isotopic labeled growth media 120.

In some embodiments, the microorganism of interest can be known or unknown and includes the microorganisms as described herein. The microorganism of interest can be introduced into the isotopically-labeled growth media 120 and/or the control growth media 130. Further, it can comprise a single, group, or a mixture of microorganisms. Almost any organism of interest could be analyzed if the organism expresses biomarker molecules and does not extensively have post-translational modification of the molecules that would impact de-convoluting the spectrum.

In some embodiments, both the isotopically-labeled growth media 120 and the control growth media 130 with one or more microorganisms can be subjected to sample growth 140 and sample processing 150. The isotopically-labeled growth media 120 can facilitate expression of biomarkers that comprise the isotopic label. Examples of suitable growth media are commercially available growth media, such as M9 and LB (available from several manufacturers, such as Fermentas, Lithuania).

The one or more microorganisms in the growth media 120 and control growth media 130 may be incubated and grown at any temperature that facilitates their growth, and preferably are grown at the same temperature in the two media. In some embodiments, microorganisms are grown at temperatures between 28-42° C. In other embodiments, the microorganisms are grown at their optimal growth temperatures. In still other embodiments, the microorganisms are grown at about 37° C.

Sample growth 140 will produce certain expressed biomarkers from the microorganism of interest. Sample growth 140 can occur by subjecting the samples to incubation or similar type processes known in the art. Sample processing 150 can utilize the isotopic labels.

In one embodiment, the system comprises a sample growth and processing module for rapid and repeatable sample preparation for MALDI MS analysis, a commercial laser desorption TOF mass spectrometer, detection and signature matching algorithms, combined with a graphical interface. In some embodiments, the sample growth and processing module has robotic capability, to facilitate the processing of multiple samples rapidly and efficiently.

In some embodiments, the system comprises a graphical user interface which enables the user to control the various modules from a single high-level user interface. In some embodiments, once the sample is fully processed in the sample growth and processing module, software instructs the user how to transfer the MALDI sample target from the sample cartridge and place it in the mass spectrometer. In some embodiments, after a single button press on the touch screen (or a single click of the mouse), the sample is then automatically analyzed and the algorithms automatically process the data. All results of the algorithmic analysis of the spectra can be summarized for the user. In some embodiments, all data, including spectra, detection scores, user-supplied sample information, and sample preparation information can be archived for future analysis.

In one embodiment of the present invention, the mass spectral acquisition module 300 (See FIG. 1) comprises matrix-assisted laser desorption/ionization (MALDI) time-of-flight (TOF) and TOF/TOF mass spectrometers. In some embodiments, other ionization sources (electrospray, DESI, etc), chromatography (HPLC, CE, etc), and mass spectrometer (single and tandem triple quad, ion trap/TOF, high resolution FTICR, etc.) equipment can be utilized in the mass spectral acquisition module 300.

In some embodiments, MALDI TOF and TOF/TOF are used for biomarker signature acquisition from both the unlabeled and labeled samples. Differentiating between drug-resistant and drug-susceptible strains by directly comparing MALDI mass spectra of two such organisms, grown in the same medium with and without drugs, is most often impossible. However, growing these same organisms in two (or more) different media—control and isotope-labeled—with and without the drug(s) present, allows differentiation to be made. For example, the drug-resistant organism will not be affected by the drug and will grow in both the unlabeled (control) and the labeled (drug-containing) media. Mass shifts will then be observed between the respective biomarkers in each organism's mass spectral signature, as illustrated and previously discussed in FIG. 3. These mass shifts are due to incorporation of different isotopes of the same element with different isotopic masses, e.g., light ($^{12}C$) versus heavy ($^{13}C$), in biomarker molecule of the organism, grown in the isotopically-enriched medium.

Thus, while real-time PCR monitors and detects the change in concentration of a specific part of a DNA molecule to discern organism growth, the present methods also monitor a change in a physical property, namely the biomarkers molecular masses, as an indication of growth. An example embodiment of a work-flow diagram for the wet-chemistry and MS data acquisition are presented schematically in FIG. 2. In addition to MALDI, other ionization methods, e.g., electrospray ionization or DESI, can be applied for detection of microorganisms and by extension biomarker mass shifts for organisms grown in isotopically-labeled media in the presence/absence of drugs.

Figure 4:
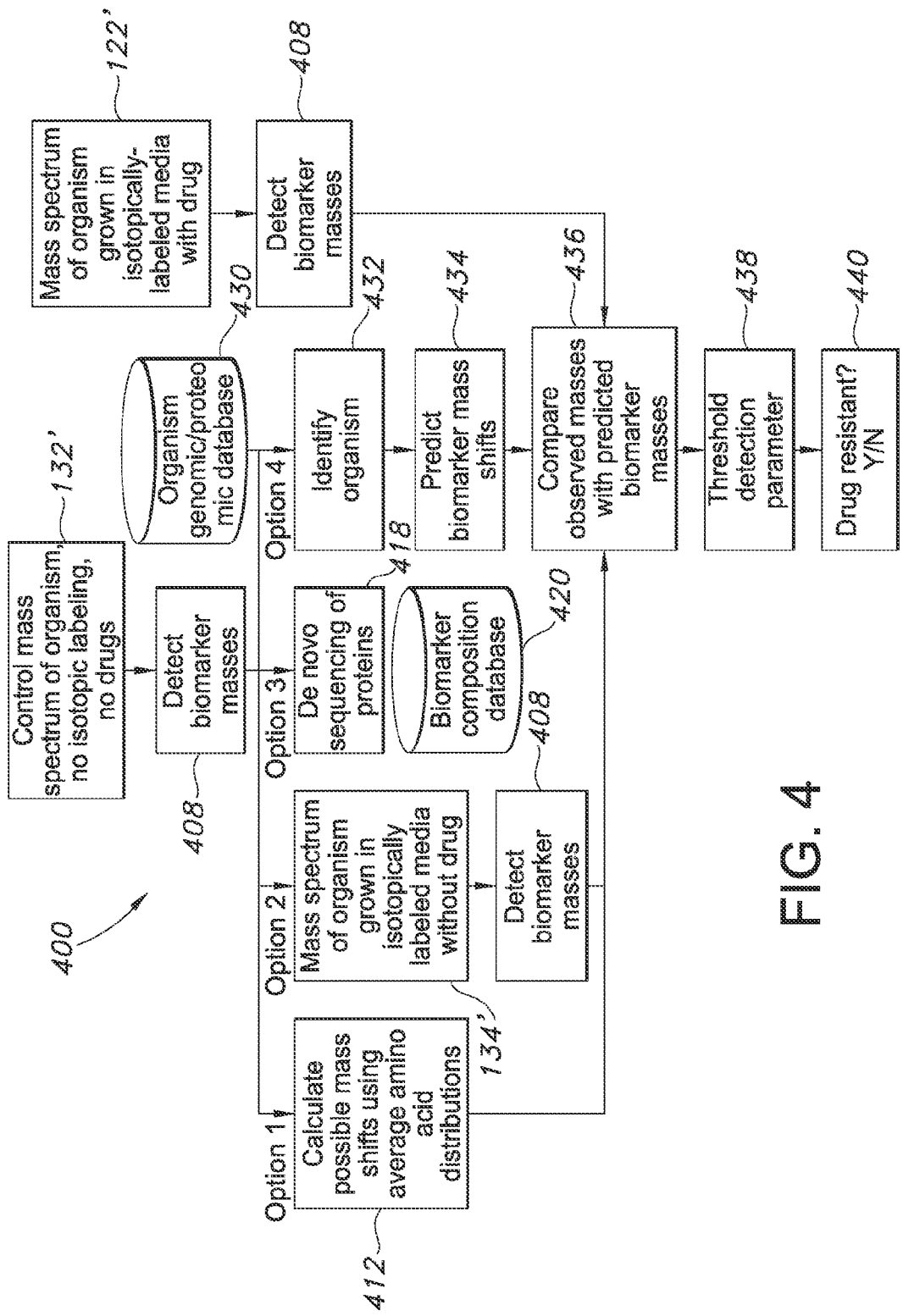
FIG. 4 shows a schematic diagram of an embodiment of the mass spectrometry-based system and method according to one example embodiment of the invention. In particular, the schematic diagram shows algorithmic module processing options that can be employed in the methods and systems of the invention.

The biomarker molecule mass shifts can be predicted from the isotope composition and ratio of different isotopes (e.g., $^{13}C$ to $^{12}C$) found in the growth medium and the actual elemental composition of the biomarkers or predicted elemental composition, based on average elemental compositions of various biomarkers, such as proteins. Several different algorithmic options can be applied for mass shift calculations, either individually or in parallel as set forth in the specification. FIG. 4 shows various embodiments for these calculations.

Figures 2A, 2B:
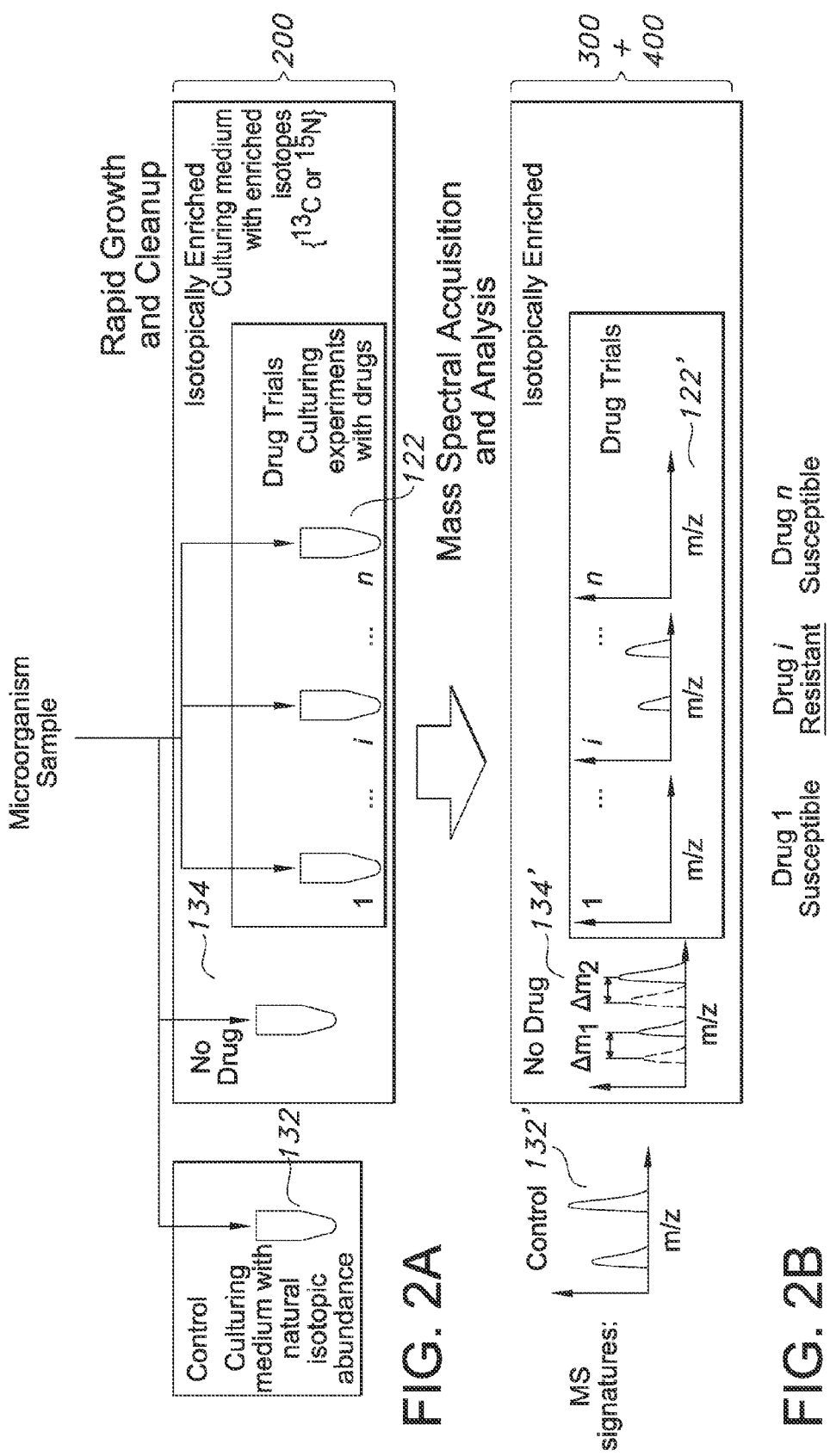
FIG. 2(B) is an embodiment showing mass spectral acquisition and analysis of the sample from 2(A).

FIG. 2A-2B show embodiments of methods and materials used in the sample growth and processing module 200, the mass spectrometry acquisition module 300, and the algorithmic module 400.

FIG. 2A shows various samples that can be used in a sample growth and processing module. These include one or more samples for drug trials 122, a no drug trial 124, and a control 132. Each of the drug trial samples 122 can comprise various levels of drug or the same level of drug, an isotopically-enriched culturing medium (e.g., $^{13}C$ or $^{15}N$) or other isotopic label and the microorganism of interest. The no drug trial 124 can comprise the same isotopically enriched medium, the microorganism of interest and no drug. The control 132 can comprise the microorganism of interest, and a culturing medium with natural isotopic abundance. The embodiments are not limited to this arrangement of samples. Other samples, combinations, and arrangements are possible and within the scope of the present embodiments. The above examples and combination are helpful for distinguishing with more certainty when a particular microorganism is drug-resistant. Each of the mentioned samples is then subject to incubation conditions that are well known in the art (sample growth and processing module 200). The samples are then all subject to mass spectral acquisition and analysis (mass spectral acquisition module 300) and algorithmic analysis (algorithmic module 400).

FIG. 2B shows the results of an embodiment of mass spectral acquisition and analysis processing steps. For instance, after the biomarker biomolecules are expressed and produced using the sample growth and processing module 200, they are subject to the mass spectrometry acquisition module 300.

In FIG. 2B, the control spectrum 132' shows the hypothetical MS signatures when a microorganism is grown in a medium with natural isotopic abundance and no drug. The no drug trial spectrum 134' and the drug trials spectra 122' are also shown in FIG. 2B. The no drug trial spectrum 134' shows the effect of the isotopic enrichment and label and the relative m/z peak shift upwards to higher m/z (spectra peaks shift to the right) when the label has been incorporated into the expressed biomolecule biomarker. In the drug trials spectra 122' the drug susceptible microorganisms show no peaks on their spectra. The drug-resistant organism shows two upshifted signature peaks (middle spectrum), which results from the incorporation of the heavier isotopic label. The control spectrum 132' provides a reference point for comparison and determination. The control spectrum 132' is particularly helpful if the final spectra do not share the same m/z ratios and/or line shapes. As a result of the analysis it can be determined whether the microorganism is resistant to the tested drug.

In another embodiment, the invention provides a method for determining the resistance of a microorganism to a drug by detecting growth of the microorganism in the presence of the drug, comprising: (a) incubating the microorganism in i) an isotopically-labeled growth medium comprising at least one drug and an isotopic label, wherein the microorganism incorporates the isotopic label into one or more biomarker molecules of the microorganism during growth in the medium; and ii) a control growth medium that lacks the drug and the isotopic label, wherein the one or more biomarker molecules of the microorganism remain unlabeled during growth in the medium; (b) applying the microorganism biomarker molecules of (a) to a mass spectrometry system to produce ion mass fragments of the biomarker molecules; (c) predicting a mass shift of the one or more unlabeled biomarker molecules of (a)(ii) using a first algorithmic analysis based on incorporation of the isotopic label of (a)(i); and (d) comparing the predicted mass shift of (c) with an observed mass of the one or more biomarker molecules of the microorganism growing in the isotopically-labeled medium with drug of (a)(i) using a second algorithmic analysis, based on which a probability that the biomarker molecules in the two media match can be determined, thereby determining the resistance of the microorganism to the drug.

The algorithms useful in accordance with embodiments of the invention accurately predict and calculate the mass shifts and compare them to experimental measurements to verify organism growth and therefore resistance to the drug. The algorithms do not require any prior knowledge/identification of the microorganism being tested, nor do they require the prior availability/acquisition of a reference mass spectrum of the microorganism and/or a library of reference mass spectra of various microorganisms. The algorithms useful in accordance with the invention help avoid very costly false positive and false negative errors. Avoiding false positive and false negative errors is critical when attempting to treat harmful microorganism infections when time is of the essence and there is little or no margin for error, e.g., choosing an ineffective antibiotic for treatment of *Bacillus anthracis*, after a bioterrorism attack.

In some embodiments of the methods and systems described herein, drug resistance/susceptibility for a variety of microorganisms and multiple drugs can be determined rapidly, preferably in 6 hours or less. The systems and methods are based on accurate bioinformatics-based prediction and experimental measurement of unique, reproducible and verifiable shifts in a fundamental physical property—molecular mass—of the constituent molecules and their specific fragments that characterize microorganisms, cultured in drug containing isotopically-labeled growth medium. Comparison of masses of characteristic biomarker molecules and their fragments, biosynthesized as a result of organism growth (rather than "lack of growth") in a set of growth media is performed by mass spectrometry (MS). In some embodiments, the methods and systems do not require any prior knowledge/identification of the microorganism being tested, nor do they require prior availability/prior acquisition of a reference mass spectrum for that organism and/or a library of reference mass spectra of that or any other organisms.

Some embodiments of the invention as described herein relate to MS of intact microorganisms and specially developed algorithms preferably to unequivocally detect organism growth in a drug-containing isotopically-labeled medium. Utilizing MS, experiments can measure the shifts in molecular mass—a fundamental physical property of matter—for organism-specific biomarker molecules, characterizing microorganisms, cultured in drug-containing isotopically-labeled growth medium.

Mass spectrometry is a well-established method for rapid characterization of microorganisms (either intact and/or lysed cells). The basic principle is the detection of organism-specific biomarker molecules, or so called "signatures." Different organisms exhibit different MS signatures, which allow differentiation between organisms to be made. Intact proteins, their proteolytic peptides, non-ribosomal peptides, lipids, DNA or other molecules have been successfully utilized as biomarkers. Sequence-specific fragments for biomarkers can be generated by tandem MS of intact proteins or proteolytic peptides, obtained after, for instance, enzymatic or chemical (increased temperature-assisted acid) hydrolysis. One method for microorganism identification by MS is generation of libraries of reference mass spectra, containing the signatures of known organisms. In some embodiments of the invention, the organism identification can be achieved without the need for a priori generation of a library of reference signature mass spectra. In this case, bioinformatics algorithms are used to compare the mass spectrum of the unknown organism to in silico generated signatures utilizing information available in genomic/proteomic databases.

In some embodiments of the methods and systems of the invention, a sample containing either known or unknown microorganism(s) is split into two (or more) portions, to be handled in the sample growth and processing module (SGPM). In some embodiments, the portions are grown for 6 hours (or less) under identical conditions in control (natural isotopic abundance) and isotopically-labeled growth media, respectively. Different stable isotopes (atoms enriched/depleted in specific isotope, e.g., $^{13}C$ or $^{15}N$, compared to the natural isotope abundance) can be used to label the medium.

A partially-labeled ("locally-labeled") medium will contain a particular growth medium component that is labeled (e.g., $^{13}$C and/or $^{15}$N labeled amino acid nutrient); a globally-labeled medium will have all growth medium molecules labeled at a predefined isotope ratio of, e.g., $^{13}$C to $^{12}$C. In some embodiments, the drug against which the organism is tested, is added at a known predetermined concentration to the isotopically-labeled medium prior to growth. In some embodiments, different drugs in a variety of concentrations can be used in a multiplexed array fashion, utilizing design-of experiments for optimization. Different media, including liquid or agar-based growth, can be used. Such media can include well-known broad spectrum-growth media or organism-specific media in cases a particular organism/drug resistance is targeted. In some embodiments, after growth, appropriate sample preparation procedures, including, e.g., cleaning by centrifugation and washing, and chromatography, can be applied to all samples—those grown in the labeled medium as well as the controls; and samples with and without the drugs present. Subsequent mass spectrometry (MS) or tandem MS examination of all microorganism samples allows the establishment of microorganism growth, i.e., organism viability/lack thereof in the presence of the drug (drug resistance/susceptibility) (as was discussed similarly in FIG. 2). To test the effect of drug dose, the sample can be split into appropriate number of portions, each of which can be grown in isotopically-enriched medium, containing the drug in different concentrations. The above procedure can be multiplexed (e.g., using a 96- or 384-well plate) to include simultaneous testing of multiple organisms/samples and multiple drugs. Also, multiple isotope labels (in addition to single ones, e.g., $^{13}$C or $^{15}$N only) can be used either simultaneously or in parallel, and allow sample "bar-coding," correlated with different drugs and/or their concentration.

The embodiments of the invention provide systems and methods for determining drug resistance of various microorganisms and pathogens. Drug resistance of a wide variety of pathogens or microorganisms can be detected by the embodiments of the present invention. Various pathogenic microorganisms are described, for example in U.S. Pat. Nos. 7,732, 586, 7,741,036, 7,850,974, 7,868,162 which disclosures relating to microorganisms are incorporated by reference herein. Exemplary, non-limiting examples of microorganisms include members of the genus *Streptococcus*, include *S. pneumonia, S. pyrogenes, S. agalactiae, S. equi, S. canis, S. bovis, S. equinus, S. anginosus, S. sanguis, S. salivarius, S. mitis, S. mutans*, and other *viridans streptococci*, members of the genus *Peptostreptococcus*, members of the genus *Enterococcus*, such as *Enterococcus faecalis* and *Enterococcus faecium*, members of the genus *Staphylococcus*, such as *Staphylococcus epidermidis, Staphylococcus aureus*, including resistant strains such as methicillin resistant *Staphylococcus aureus* (MRSA), members of the genus *Hemophilus*, such as *Hemophilus influenzae*, members of the genus *Pseudomonas*, such as *Pseudomonas aeruginosa, Pseudomonas pseudomallei, Pseudomonas mallei*, members of the genus *Brucella* such as *Brucella melitensis, Brucella suis* and *Brucella abortus*, members of the genus *Bordetella*, such as *Bordetella pertussis*, members of the genus *Bacillus*, including pathogenic members such as *Bacillus anthracis* and *Bacillus cereus*, members of the genus *Clostridium*, such as *Clostridium difficile, Clostridium botulinum, Clostridium tetani, Clostridium perfringens*, members of the genus *Neisseria*, such as *Neisseria meningitidis* and *Neisseria gonorrhoeae*, members of the genus *Moraxella*, such as *Moraxella catarrhalis*, members of the genus *Mycobacterium*, including *Mycobacterium tuberculosis, Mycobacterium bovis, Mycobacterium bovis* BCG, *Mycobacterium africanum, Mycobacterium canetti, Mycobacterium caprae, Mycobacterium microti*, and *Mycobacterium pinnipedii*, members of the genus *Corynebacterium*, such as *Corynebacterium diphtheriae, Corynebacterium ulcerans, Corynebacterium pseudotuberculosis, Corynebacterium pseudodiphtheriticum, Corynebacterium urealyticum, Corynebacterium hemolyticum* and *Corynebacterium equi*, members of the genus *Listeria*, such as *Listeria monocytogenes*, members of the genus *Nocardia*, such as *Nocardia asteroides*, members of the genus *Bacteroides*, members of the genus Actinomycetes, members of the genus *Treponema*, such as *Treponema pallidum*, and members of the genus *Leptospirosa* and related organisms.

The embodiments of the invention may also be useful in detecting drug resistance of various gram negative bacteria such as members of the genus *Klebsiella*, including *pneumoniae*, members of the genus *Salmonella*, such as *Salmonella enterica, Escherichia coli* including serotype O157:H7, members of the genus *Francisella*, such as *Francisella tularensis*, members of the genus *Proteus*, members of the genus *Serratia*, members of the genus *Acinetobacter*, members of the genus *Yersinia*, such as *Yersinia pestis*, members of the genus *Francisella*, such as *Francisella tularensis*, members of the genus *Enterobacter*, members of the genus *Bacteroides*, members of the genus *Legionella* and the like. In some embodiments, drug-resistant forms of *Chlamydia* are detected, such as *Chlamydia trachomatis, Chlamydia psittaci* or *Chlamydia pneumoniae*, for example.

In addition, the embodiments may prove useful in detecting drug resistance of various protozoan or macroscopic organisms such as *Cryptosporidium, Isospora belli, Toxoplasma gondii, Trichomonas vaginalis, Cyclospora* species, for example.

In some embodiments antibiotic-resistant bacteria are detected that include *Staphylococci* (methicillin-resistant strains), vancomycin-resistant *enterococci* (*Enterococcus faecium*), and resistant *Pseudomonas aeruginosa*.

The microorganism can be isolated from a biological or environmental sample prior to analysis. In some embodiments the microorganisms are found on surfaces, in food, in biological fluids, such as saliva, urine, fecal matter, blood, lymph, or plasma, on materials used to wipe surfaces suspected of containing organisms, in hair, objects handled or contacted by organisms, etc. In some embodiments, the microorganisms can be genetically-engineered, mutated, transformed, altered or modified and tested for drug resistance.

The antibiotic that can be tested for resistance is not limiting. In some embodiments, the antibiotic(s) selected for a microorganism will depend on a number of factors, such as whether the microorganism is known, knowledge about known resistances among the strains of the microorganism to various antibiotics or known classes of antibiotics, or whether the bacteria is gram-negative or gram-positive, for example. Examples of particular classes of antibiotics to be tested include, for example, aminoglycosides (e.g., tobramycin, amikacin, gentamicin, kanamycin, netilmicin, tobramycin, streptomycin, azithromycin, clarithromycin, erythromycin, erythromycin estolate/ethylsuccinate, gluceptate/lactobionate/stearate), beta-lactams such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin and piperacillin), cephalosporins (e.g., cephalothin, cefazolin, cefaclor, cefamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin), fluoroquinolones (e.g., ciprofloxacin), carbepenems (e.g., imipenem), tetracyclines (e.g., doxycycline, minocycline, tetracycline), macrolides (e.g., erythromycin and clarithromycin), monobactams (e.g., aztreonam), quinolones (e.g., fleroxacin, nalidixic acid, norfloxacin, ciprofloxacin, ofloxacin, enoxacin, lomefloxacin and cinoxacin), glycopeptides (e.g., vancomycin, teicoplanin), chloramphenicol, clindamycin, trimethoprim, sulfamethoxazole, nitrofurantoin, rifampin and mupirocin, and polymyxins, such as PMB, oxazolidinones, and phenyloxazolidinones derivatives as described in U.S. Pat. No. 7,592,335, the disclosure of which phenyloxazolidinones derivatives are incorporated by reference herein.

Different drugs in a variety of concentrations can be used in a multiplexed array fashion, utilizing design of experiments for optimization. For example, multiple drugs, combinations of drugs, and different concentrations of drugs can be tested simultaneously against a microorganism sample.

The media used to grow the microorganisms can be any isotopically-labeled media, including, for example, commercially available media. In some embodiments, the media is BioExpress 1000 growth media available from Cambridge Isotope Laboratories, Inc. Andover, Mass. The media is comprised of a complex mixture of glucose, amino acids, peptides, vitamins, minerals and cofactors. BioExpress 1000 is supplied as a 100 mL sterile liquid concentrate (10×), and reconstitutes to 1 L with no final pH adjustment required. In one embodiment, the control media used is BioExpress 1000 growth media ($^{13}C$ natural isotopic abundance): CGM-1000-U-S (unlabeled, 10× concentrate), and the isotopically-labeled media is BioExpress 1000 growth media ($^{13}C$ isotopically-enriched growth media): CGM-1000-C-S ($^{13}C$—98%, 10× concentrate). Other isotopically-labeled BioExpress 1000 growth media include ($^{15}N$ isotopically-enriched growth media): CGM-1000-M ($^{15}N$—98%, 10× concentrate), as well as CGM-1000-CN ($^{13}C$—98%; $^{15}N$—98%, 10× concentrate). Alternative growth media also are available from the same supplier, including Celtone Complete Medium, which is a rich bacterial cell growth medium derived from an algal source with a growth rate comparable to LB media. Celtone contains amino acids, nucleic acids, peptides, vitamins, salts and other essential nutrients and provides cell growth and high protein expression. Celtone Complete media include: CGM-1040-C ($^{13}C$, 98%), CGM-1040-N ($^{15}N$, 98%), CGM-1040-CN ($^{13}C$, 98%; $^{15}N$, 98%), and CGM-1040-U (unlabeled). Another alternative growth medium is Celtone Base Powder medium, which is a mixture of amino acids, peptides, vitamins and other essential nutrients, and provides an environment for bacterial cell growth and high protein expression. Celtone Base Powder media include: CGM-1030P-C ($^{13}C$, 98%), CGM-1030P-N ($^{15}N$, 98%), CGM-1030P-CN ($^{13}C$, 98%; $^{15}N$, 98%), and CGM-1030P-U (unlabeled). Still yet another alternative growth medium is Spectra 9 for bacterial growth and protein expression. It is comprised of labeled salts and labeled carbohydrates, and is supplemented with Celtone Base Powder (1 g powder per liter Spectra 9), as described above. Spectra 9 media include: CGM-3030-C ($^{13}C$, 98%), CGM-3030-N ($^{15}N$, 98%), CGM-3030-CN ($^{13}C$, 98%; $^{15}N$, 98%), and CGM-3030-U (unlabeled).

Biomarkers

In accordance with example embodiments of the invention, mass spectrometry is used to detect one or more various organism-specific biomarker molecules, or "signatures." In general, microorganisms introduced intact in a mass spectrometer generate unique signatures that allow taxonomic distinctions to be made between different organisms (see, e.g., Demirev et al. *J. Mass Spectrom.* 2008, 43, 1441-1457; Demirev et al. *Annu. Rev. Anal. Chem.* 2008, 1, 71-94.).

Different organisms and biomarkers exhibit different mass spectrometry signatures or peaks, which allow differentiation between different organisms and biomarkers to be made. Any source of biomarkers can be used in accordance with example embodiments of the present invention, including a biological agent, microorganisms, including intact microorganisms or subcellular or extracellular parts or mixtures thereof, a cell culture or isolate thereof, isolated or fractionated proteins, their proteolytic peptide fragments, peptides, lipopeptides, non-ribosomal peptides, ribosomal proteins, lipids, phospholipids, oligosaccharides, polysaccharides, DNA, RNA, or other molecules, or combinations thereof can be subjected to mass spectrometry in accordance with example embodiments of the present invention. In some embodiments, the biomarkers detected and analyzed by mass spectrometry are highly abundant proteins, such as ribosomal proteins.

Biomarkers, such as proteins can be extracted from intact or treated materials. In some embodiments, the biomarker molecule is isolated from the microorganism cell or fractionated from other molecules prior to mass spectrometry. In other embodiments, the intact microorganism or a part thereof containing the biomarker is subjected to mass spectrometry. In some embodiments, an intact microorganism is subjected to mass spectrometry, yielding a spectrum containing several peaks, each peak characteristic of a specific biomarker, and the spectrum as a whole constituting the microorganism's mass spectrometry "signature." In some embodiments, the biomarker is excreted into the cell medium, and the cell culture media or purified part thereof can be subjected to mass spectrometry to detect the excreted biomarker.

In some embodiments, the biomarkers are fragmented to smaller sizes prior to mass spectrometry. In some embodiments, protein biomarkers are partially digested into smaller peptides. The proteins can be partially digested with one or more enzymes, such as trypsin, subtilisin, chymotrypsin, pepsin, papain, *S. aureus* V8, elastase, Lys-C endoproteinase, Arg-C endoproteinase, Glu-C endoproteinase enzymes, or a combination thereof. The enzymes can be chemically-modified and/or immobilized, for example, on tiny beads or on a surface to minimize autolysis.

In one embodiment such as MS or MS/MS (tandem mass spectrometry), rapid detection of microorganisms is achieved by detecting the unique biomarkers of expressed proteins of the microorganism of each particular species. In some embodiments, the observed biomarkers are highly expressed proteins with house-keeping functions, such as ribosomal, chaperone, and transcription/translation factor proteins. In some embodiments, the biomarkers comprise lipids, lipoproteins, peptides, and other similar types or molecules or combination of molecules. In one embodiment the biomarker can comprise an isotopically-labeled protein. In another embodiment it can comprise an isotopically-labeled protein, peptide, lipoprotein, lipopeptide, or lipid. Other possible biomarker biomolecules may be used for detection and characterization in the present embodiments. Any biomarker may be employed, which preferably is expressed by the microorganism and which also preferably produces a distinguishable MS signature.

In some embodiments, the biomarker proteins are about 100 kDa in size or less. In some embodiments, the biomarker proteins are about 80 kDa in size or less, about 70 kDa in size or less, about 60 kDa in size or less, about 50 kDa in size or less, about 40 kDa or less, about 30 kda or less, about 20 kDa or less, or about 10 kDa or less. In some embodiments, the number and type of expressed proteins can be fairly limited and within predictable size ranges. In prokaryotes, generally expressed proteins do not undergo as extensive post-translational modifications as are present in eukaryotic organisms. This makes prokaryotes and bacteria of particular interest for study using MS techniques. Expressed proteins can generally be above a certain signal to noise ratio in the MS. For instance, in many cases the expressed proteins will be in high enough abundance to exceed a threshold signal-to-noise intensity level of at least 3. In some embodiments, the threshold signal-to-noise intensity level is at least 2, 3, 4, 5 or 6. This is because the abundance of the expressed proteins and protein fragments will be higher than other low-expression-level-proteins and/or protein fragments. In some embodiments, these characteristics provide a window for studying microorganism using a "top down" proteomics approach.

Isotopic Tags & Labeling

In one embodiment of the invention various isotopic tags can be incorporated into the medium used to grow the microorganism of interest. Isotopes are atoms that contain the same number of protons, but different number of neutrons, in their nuclei. These atoms all share similar chemical properties, which is largely due to the fact that isotopes share a common electronic configuration. Isotopes can be employed for various purposes. Elements can have both stable and unstable isotopes. In some embodiments, the isotope used in example embodiments of the invention is a stable isotope. For instance, many of the stable and useful isotopes occur in the first three periods of the periodic table. In some embodiments, isotopes of carbon, nitrogen, phosphorus, and sulfur or a combination thereof are used in example embodiments of the invention. In some embodiments, the isotopic label is selected from the group consisting of $^2D$, $^{13}C$, $^{15}N$ and $^{18}O$.

Mass Spectrometers & Detectors

The microorganism or biomarker sample is subjected to mass spectrometry analysis. The sample can be processed and subjected to mass spectrometry using standard techniques and procedures. The following articles relate to mass spectrometry sample preparation, processing, and analysis and have been reported in the scientific literature, all of which are incorporated herein by reference in their entirety: P. Demirev, C. Fenselau, *Annual Reviews in Analytical Chemistry* 1 (2008) 71-94, "Mass spectrometry for rapid characterization of microorganisms"; P. Demirev, C. Fenselau, *J. Mass Spectrom.* 43 (2008) 1441-1457, "Mass spectrometry in biodefense"; Doroshenko, V. M.; Laiko, V. V.; Taranenko, N. I.; Berkout, V. D.; Lee, H. S. (2002), "Recent developments in atmospheric pressure MALDI mass spectrometry" *Int. J. Mass Spectrom.* 221: 39-58; Eng, J. K., A. L. McCormack, et al. (1994). "An approach to correlate tandem mass spectral data of peptides with amino acid sequences in a protein database." *Journal of the American Society for Mass Spectrometry* 5(11): 976-989; Fenselau, C. and P. A. Demirev (2001). "Characterization of intact microorganisms by MALDI mass spectrometry." *Mass Spectrom. Rev.* 20(4): 157-171; Harris, W. A. and J. P. Reilly (2002). "On-Probe Digestion of Bacterial Proteins for MALDI-MS" *Anal. Chem.* 74(17): 4410-4416; Hooker, J. M., E. W. Kovacs, and M. B. Francis, Interior surface modification of bacteriophage MS2. *J Am Chem Soc,* 2004. 126(12): p. 3718-9; Karas, M. and F. Hillenkamp (1988). "Laser desorption ionization of proteins with molecular masses exceeding 10000 Daltons." *Anal. Chem.* 60(20): 2299-2301; Krishnamurthy, T. and P. L. Ross (1996). "Rapid identification of bacteria by direct matrix-assisted laser desorption/ionization mass spectrometric analysis of whole cells." *Rapid Commun. Mass Spectrom.* 10: 1992-1996.; Krutchinsky, A. N., M. Kalkum, et al. (2001). "Automatic Identification of Proteins with a MALDI-Quadrupole Ion Trap Mass Spectrometer." *Anal. Chem.* 73: 5066-5077; Perkins, D. N., D. J. Pappin, et al. (1999). "Probability-based protein identification by searching sequence databases using mass spectrometry data." *Electrophoresis* 20(18): 3551-67; Pribil P A, Patton E, Black G, Doroshenko V, Fenselau C. (2005), "Rapid characterization of *Bacillus* spores targeting species-unique peptides produced with an atmospheric pressure matrix-assisted laser desorption/ionization source." *J Mass Spectrom.* 40(4): 464-474; Strauss, J. H., Jr. and R. L. Sinsheimer, Purification and properties of bacteriophage MS2 and of its ribonucleic acid. *J Mol Biol,* 1963. 7: p. 43-54; Tanaka, K., H. Waki, et al. (1988). "Protein and polymer analyses up to m/z 100,000 by laser ionization time-of-flight mass spectrometry." *Rapid Commun. Mass Spectrom.* 2: 151-153; Warscheid, B., and Fenselau, C. (2003). "Characterization of *Bacillus* Spore Species and Their Mixtures Using Postsource Decay with a Curved-Field Reflectron," *Anal. Chem.* 75(20): 5618-5627.

For MALDI-TOF, a number of sample preparation methods can be utilized including but not limited to, dried droplet (Karas and Hillenkamp, *Anal. Chem.,* 60:2299 2301, 1988), vacuum-drying (Winberger et al., *In Proceedings of the 41st ASMS Conference on Mass Spectrometry and Allied Topics,* San Francisco, May 31 Jun. 4, 1993, pp. 775a b), crush crystals (Xiang et al., *Rapid Comm. Mass Spectrom.,* 8:199 204, 1994), slow crystal growing (Xiang et al., *Org. Mass Spectrom,* 28:1424 1429, 1993); active film (Mock et al., *Rapid Comm. Mass Spectrom.,* 6:233 238, 1992; Bai et al., *Anal. Chem.,* 66:3423 3430, 1994), pneumatic spray (Kochling et al., *Proceedings of the 43rd ASMS Conference on Mass Spectrometry and Allied Topics;* Atlanta, Ga., May 21 26, 1995, p 1225); electrospray (Hensel et al., *Proceedings of the 43rd ASMS Conference on Mass Spectrometry and Allied Topics;* Atlanta, Ga., May 21 26, 1995, p 947); fast solvent evaporation (Vorm et al., *Anal. Chem.,* 66:3281 3287, 1994); sandwich (Li et al., *J. Am. Chem. Soc.,* 118:11662 11663, 1996); and two-layer methods (Dai et al., *Anal. Chem.,* 71:1087 1091, 1999). See also, e.g., Liang et al., *Rapid Commun. Mass Spectrom.,* 10:1219 1226, 1996; van Adrichem et al., *Anal. Chem.,* 70:923 930, 1998. For example, samples of microorganisms can be lyophilized, solubilized, extracted into a solution, such as a 70:30 solution of $CH_3CN$:0.1% trifluoroacetic acid, and then embedded in the matrix. Various matrices can be used, e.g., sinapinic acid, 2,5-dihydroxybenzoic acid, alpha-cyano-4-hydroxycinaminnic acid. A sample can be processed in various ways prior to addition to the matrix. For example, the sample can be extracted, subjected to corona discharge, chromatography, such as HPLC, etc., e.g., to remove particular unwanted constituents (such as lipids, small molecules, high molecular weight constituents) before mass spectrometry.

In some embodiments, sample processing includes several steps, such as protein biomarker extraction (usually using specific solvent), protein digestion, on-probe sample cleanup, and MALDI matrix deposition and can includes several steps of sample liquid evaporation. In some embodiments, samples preparation time can be minimized by optimizing various parameters as described by U.S. Pat. No. 7,858,392, incorporated by reference herein. In some embodiments, the sample can be processed directly on the sample holder (e.g., a probe or a MALDI plate).

The mass spectrometry acquisition module (MSAM) (See, e.g., FIG. 1) comprises a mass spectrometer system. In some embodiments, the mass spectrometer system can comprise an ion source, an optional ion focusing or separation device, and a detector.

Various mass spectrometers have been developed and can be employed with the present embodiments. Mass spectrometers detect the ions or fragments that are produced by the ion sources. Essentially, mass spectrometers measure the mass-to-charge ratio of biomolecular analytes such as peptides, proteins, lipids, carbohydrates, nucleic acids or peptide fragments.

Various ion sources are known and used in the art. The ion source is the part of the mass spectrometer that ionizes the material under analysis (the analyte). The ions are then transported by magnetic or electric fields. The ion source that can be employed in accordance with example embodiments of the invention is non-limiting. Electron ionization and chemical ionization are used for gases and vapors. In chemical ionization sources, the analyte is ionized by chemical ion-molecule reactions during collisions in the source. Two techniques often used with liquid and solid biological samples include electrospray ionization (ESI) and matrix-assisted laser desorption/ionization (MALDI).

MALDI and ESI allow for the transfer of large non-volatile molecules into the gas phase. In MALDI, an appropriate photo-absorbing organic compound (matrix) is mixed with the sample (e.g., intact microorganism) prior to introduction into the mass spectrometer. The sample is then irradiated with a pulsed ultraviolet or infrared laser that desorbs high-mass bio-molecular ions for subsequent MS analysis.

In ESI, large, multiply charged ions can be generated by transporting the analyte solution through a capillary needle that is maintained at a desired voltage relative to ground.

In some embodiments, the ion source is selected from the group consisting of electrospray ionization (ESI), matrix-assisted laser desorption/ionization (MALDI), fast atom ion bombardment (FAB), chemical ionization (CI), atmospheric pressure photon ionization (APPI), atmospheric pressure chemical ionization (APCI), atmospheric pressure matrix assisted laser desorption ionization (AP-MALDI). These ion sources are not limiting, and other ion sources can be employed in accordance with example embodiments of the present invention. The ion sources can be under vacuum or at atmospheric pressure absent a vacuum.

The optional ion focusing or separation device can comprise any necessary mass analyzers such as quadrupoles, ion mirrors, housings, or other components that can be employed to separate the ions of interest.

Mass analyzers can be used alone, or in combination to form tandem mass spectrometers. In the latter case, a first mass analyzer can be use to separate the biomarker ions (precursor ion) from each other and determine the molecular weights of the various biomarker constituents in the sample. A second mass analyzer can be used to analyze the separated constituents, e.g., by fragmenting the precursor ions into product ions, such as smaller peptide ions in the case of protein biomarkers. Any desired combination of mass analyzers can be used, including, e.g., triple quadrupoles, tandem time-of-flights, ion traps, and/or combinations thereof.

Any combination of ion source, ion focusing and/or separation device and detector can be employed with the present embodiments. Separations of biomarkers by mass spectrometry can be accomplished using one or more different techniques. In some embodiments, separations can be accomplished using time-of-flight (TOF MS), separation by quadrupole electric fields, by ion mobility (drift in a gas), or separation by ion trapping. In some embodiments, for structural analysis of various biomolecules such as peptides, mass spectrometry separations can be accomplished in MS mode or MS/MS, where one or more techniques are used in tandem. In some embodiments, either MALDI or ESI can be coupled with one or more of these techniques to accomplish separations. In some embodiments, MALDI is coupled with TOF. In one embodiment of a MALDI/TOF experiment, analytes are deposited on a surface and then irradiated by a laser to produce an "ion plume." The ions then are accelerated to a fixed amount of kinetic energy and directed down a flight tube. The various ions have differing velocities since they differ in size and mass. Once at the end of the flight tube the ions are then reversed or reflected using a reflector prior to being detected by a detector. Other ion sources, separation devices and detectors can be employed with the embodiments of the present invention, in varying combinations. In some embodiments, mass spectrometry systems can comprise TOF, TOF/TOF, AP-MALDI, ion trap, quadrupole, triple quadrupole, FTICR, Orbitrap, electric and magnetic mass analyzers, ion mobility devices, or their combination.

In some embodiments, the microorganisms are introduced intact in a mass spectrometer to generate unique signatures that allow for taxonomic distinctions to be made between different microorganisms. In some embodiments, one or more biomarkers are isolated from the microorganisms prior to performing mass spectrometry.

In some embodiments, sequence-specific fragments for biomarkers are generated by tandem MS of intact proteins or proteolytic peptides, obtained after, for example, enzymatic or chemical (elevated temperature-assisted acid) hydrolysis. In some embodiments, libraries of reference mass spectra signatures from various microorganisms are obtained, and used to facilitate identification of an unknown microorganism. Bioinformatics algorithms are used to compare the mass spectrum of the sample to a reference sample, which can include in silico generated signatures of microorganisms or specific biomarkers utilizing information available in genomic and/or proteomic databases.

In some embodiments, the mass spectrometer is equipped with commercial software that identifies peaks above a certain threshold level, calculates mass, charge, and intensity of detected ions. Correlating molecular weight with a given output peak can be accomplished directly from the spectral data, i.e., where the charge on an ion is one and the molecular weight is therefore equal to the numerator value minus the mass of the ionizing proton. However, protein ions can be complexed with various counter-ions and adducts, such as $Na^+$, and $K^+$. In such a case, it would be expected that a given protein ion would exhibit multiple peaks, such as a triplet, representing different ionic charge states of the same protein. Thus, it may be necessary to analyze and process spectral data to determine families of peaks arising from the same protein. This analysis can be carried out conventionally, e.g., as described by Mann et al., *Anal. Chem.*, 61:1702 1708, 1989.

Algorithms

In accordance with the embodiments as described herein, drug resistance is determined by algorithmic analysis which comprises predicting a characteristic mass shift and comparing the predicted mass shift with an observed mass shift of one or more biomarkers from a microorganism growing in isotopically-labeled media with drug. In some embodiments, the algorithms that can be used in accordance with example embodiments of the invention are shown in FIG. 4 (listed as Options 1-4) and are discussed below.

Referring now to FIG. 4, the process steps of the algorithmic module 400 will now be described in more detail. The algorithmic module 400 can employ the algorithms 410 to interpret the mass spectrometry results. The results will generally be in the form of many different predicted mass shift values for the various biomarkers (Δm values). In some embodiments set forth below, the algorithms 410 can be employed to compare the Δm values of the mass spectroscopy acquisition module 300 to in silico generated Δm values of the biomarker composition database 420 and/or the organism genome/proteome database 430. The assignment of the correct biomarker and mass can then be accomplished.

The embodiments should not be interpreted to be limited to the disclosed algorithms. The disclosed algorithms provide confidence in matches made between various generated mass spectrometry ion fragments from the isotopically-labeled or enriched fragments and the control fragments (mass shifts, Δm). The algorithms help in accurately determining mass shifts, making correct assignment of mass shifts to biomarkers, and determining drug resistance. In assigning mass shifts (or Δm) to biomarkers various algorithms can be employed.

Referring to FIGS. 2 and 4, a control mass spectrum 132' and an isotopically-labeled mass spectra 134' (no drug trial spectrum 134') can be compared by various algorithmic analyses with an isotopically-labeled drug trial spectra 122' to determine drug resistance 440. Since the control mass spectrum 132' is important for determining and calculating and/or predicting mass shifts, a number of options (options 1-4) are provided to increase the accuracy of the predictions of biomarker masses and confirming the biomarker mass shifts 436 as they compare and correlate to the isotopically-labeled spectra 122'. Further, wrong correlations or comparisons can lead to incorrect mass assignments which in the end could give overall incorrect results in determining microorganism drug resistance 440. Further, in some embodiments where an unknown microorganism is tested, in silico comparisons to increase predictions and accuracy can be made.

Option 1

In one embodiment, control biomarker mass shifts 132' can be determined by calculating a range of possible mass shifts using average amino acid distributions (in the case of protein biomarkers), or fatty acid chain lengths in the case of lipids. A generic model based on the average molecular weight and elemental composition of a statistically-determined "average" biopolymer building block (for peptides/proteins—"averagine," for DNA—"averabaseine") can be used to predict mass shifts for unknown biomarkers/organisms—See FIG. 3 and Example 1, below. In this embodiment, a range of mass shift values for each control protein biomarker can be estimated by taking the two limiting-amino acid cases, e.g., the amino acid with least number of C-atoms per mass and the one with the highest number per mass, for the case of $^{13}$C-labeling.

In some embodiments, the average elemental composition for an amino acid is $C_{4.9384}H_{7.7583}N_{1.3577}O_{1.4773}S_{0.0417}$, which yields $M_{ave}$=111.1254 Da for an average amino acid in any give protein. In some embodiments, the ratios of $^{13}$C to $^{12}$C are 0.01 and 46, for natural abundance and isotopically-labeled media, respectively. Using this information, an average elemental composition can be determined for a protein with a known molecular weight as determined by mass spectrometry, e.g., an average number of candidate carbons in a protein that are candidates for isotopic labeling. A predicted mass shift can be calculated based on this information. The differences between observed and predicted mass shifts are due to difference between actual and predicted number of C-atoms in a molecule.

Option 2

In one embodiment, the algorithm comprises growing the microorganism, without the drug present, in the isotopically-labeled medium, yielding candidate novel peaks that can be shifted from observed control spectrum peaks. These peaks are used to predict mass shifts of biomarkers growing in the isotopically-labeled media in the presence of the drug.

Option 3

In another embodiment, control mass shifts 132' (See FIG. 3) can be calculated using biomarker composition databases 420 (See FIG. 4). For instance, biomarker composition databases 420 can be interrogated for accurate control of biomarker mass shifts 132'. The biomarker composition databases can be generated as a result of de novo sequencing of proteins 418.

In some embodiments, MS and tandem MS utilizing (most often) high resolution MS instrumentation (see, e.g., Demirev et al., *Analyt. Chem.* 73 (2001) 5725-5731, "Tandem mass spectrometry of intact proteins for characterization of biomarkers from *Bacillus cereus* T spores") can be used for de novo sequencing of individual biomarker molecules of a microorganism. Knowing the sequence allows the determination of the amino acid composition of small peptides and proteins without interrogation of any type of public or private pre-existing biomarker database. Non-ribosomally synthesized biomarkers (e.g., lipopeptides) can be also identified and their structures elucidated and their elemental compositions established by tandem MS.

In some embodiments, the biomarkers are de novo sequenced using either a "bottom up," or "top-down" proteomic analysis. In "top down" proteomics, an intact precursor protein is identified by deducing its partial amino acid sequence after fragmentation in a tandem MS experiment. In some embodiments, top-down proteomics does not require protein biomarker enrichment and separation prior to analysis. In some embodiments, the biomarkers are de novo sequenced from intact microorganisms, either in pure form or in mixture with other microorganisms.

In some embodiments, dissociation of precursor protein ions results in sequence-specific backbone cleavages, with spectra dominated by ions formed by cleavages on the C-terminal side of aspartic or glutamic acid residues. In some embodiments, the amino acid composition of the biomarker can be obtained without reference to any type of biomarker database.

Similar to the "top-down" proteomics methodology for microorganism identification, the "bottom-up" approaches are based on initial identification of individual proteins. In bottom-up proteomics, however, proteolysis (enzymatic digestion) of the proteins is first performed, resulting in several peptide fragments ("proteolytic" peptides) from each protein. In some embodiments, experimentally measured masses of proteolytic peptides, generated in situ by rapid residue-specific cleavages, can be mapped to biomarker databases for direct biomarker identification. In some embodiments, it is not necessary to interrogate a known biomarker database to obtain the sequence of the biomarker.

In some embodiments, the specificity of the proteolytic enzymes, complementary to or concurrently with peptide sequence tag information obtained by tandem mass spectrometry, can be used to unequivocally identify the protein of interest.

In all these cases, the control mass shifts can be directly calculated/predicted from the protein amino acid sequences and/or the elemental compositions of the respective biomarkers.

Option 4

In another embodiment, control biomarker mass shifts 132' (See FIG. 3) can be calculated using one or more organism genome/proteome databases. The molecular weights of the protein constituents determined by the control spectrum can then be used to query databases which contain, among other information, lists of protein molecular weight information and the identity of the organism source from which the information was derived. By comparing the set of protein molecular masses of an unknown, as determined, for instance, in a mass spectrum, against a database containing the molecular masses of proteins present in known organisms, the unknown can be rapidly and reliably identified, classified, or characterized. In this embodiment, mass spectral peaks of the control spectrum can be assigned to proteins in the database, yielding the amino-acid composition associated with each peak. The expected shift in protein mass due to the isotopes can be calculated directly and compared with the mass spectrum of microorganism grown in the isotopically-labeled media with the drug.

MS and tandem MS (utilizing both low and high resolution MS instrumentation) can be used for individual biomarker molecule and intact microorganism identification by interrogation of one or more genome/proteome databases. Various bioinformatics algorithms have been developed for microorganism detection and presumptive identification by mass spectrometry and genome/proteome database searches (see, e.g., Demirev et al. *Analytical Chemistry* 77 (2005) 7455-7461, "Top-down proteomics for rapid identification of intact microorganisms"; Demirev et al., *Analyt. Chem.* 71 (1999), 2732-2738, "Microorganism identification by mass spectrometry and protein database searches"; Demirev, F. Pineda, J. Lin, C. Fenselau, *Analyt. Chem* 73 (2001) 4566-4573, "Bioinformatics and mass spectrometry for microorganism identification: proteome-wide post-translational modifications and database search algorithms for characterization of intact *H. pylori*"; Demirev et al. *Johns Hopkins APL Technical Digest,* 25 (2004) 27-37, "Bioinformatics-based strategies for rapid microorganisms identification by mass spectrometry" Demirev et al., U.S. Pat. No. 7,020,559; Demirev et al., Analyt. Chem. 73 (2001) 5725-5731, "Tandem mass spectrometry of intact proteins for characterization of biomarkers from *Bacillus cereus* T spores" all of which are incorporated herein in their entirety).

In some embodiments of this algorithmic option, tandem mass spectrometry, such as MALDI TOF/TOF is applied for rapid and high-confidence identification of biomarkers from various species using a "top-down" proteomics approach. In some embodiments, fragment ion spectra of whole (undigested) protein biomarkers is obtained and laser-induced dissociation (unimolecular decay) of higher mass (>5 kDa) precursor ions in the first TOF analyzer is followed by reacceleration and subsequent high-resolution mass analysis of the resulting sequence-specific fragments in a reflectron TOF analyzer. The experimental MS/MS spectrum is then compared with in silico-generated tandem mass spectra from all protein sequences contained in one or more genomic/proteome databases, with masses within a preset range around the precursor ion mass. In some embodiments, a "bottom-up" proteomics approach can be used, wherein peptide fragments are generated by enzymatic digestion (for example, by trypsin) of the biomarker proteins, and the enzymatic fragments are identified by comparison with in silico generated enzymatic (e.g., tryptic) fragments from all protein sequences contained in one or more genomic/proteome databases. Regardless of the approach used, a p-value, the probability that the observed matches between experimental and in silico-generated fragments occur by chance, can be computed and used to rank the database proteins to identify the most plausible precursor protein. The probabilistic algorithms discussed herein can be used to measure the degree of match between the experimental and in silico generated biomarkers. By inference, the source microorganism is then identified on the basis of the identification of individual, unique protein biomarker(s). Once a match is determined from the database, the predicted mass shift can be calculated.

In some embodiments, the database searched is the SwissPROT/TrEMBL proteome databases (Bairoch, A.; Apweiler, R.; Wu, C. H.; Barker, W. C.; Boeckmann, B.; Ferro, S.; Gasteiger, E.; Huang, H.; Lopez, R.; Magrane, M.; Martin, M. J.; Natale, D. A.; O'Donovan, C.; Redaschi, N.; Yeh, L. S. *Nucleic Acids Res.* 2005, 33, D154-159) to extract precursor protein sequences with masses within a preset range around the precursor ion mass (e.g., ±2.5 Da). In some embodiments, the probability of a posttranslational protein modification, such as N-terminal Met truncation, can be incorporated (see, e.g., Pineda, F.; Antoine, M.; Demirev, P.; Feldman, A.; Jackman, J.; Longenecker, M.; Lin, *J. Anal. Chem.* 2003, 75, 3817-3822; Demirev, P.; Lin, J. S.; Pineda, F. J.; Fenselau, C. *Anal. Chem.* 2001, 73, 4566-4573, the disclosures of the probability of a posttranslational protein modification are incorporated by reference herein).

In some embodiments of this algorithmic option, the microorganism is present in a mixture of microorganisms. In some embodiments, tandem mass spectrometry coupled with algorithmic analysis enables deconvolution of a mixture of organisms to identify individual organisms and biomarkers in the mixture.

Various databases can be useful in accordance with example embodiments of the present invention. Useful databases include databases which contain genomic sequences, expressed gene sequences, and/or expressed protein sequences. In some embodiments the databases contain nucleotide sequence-derived molecular masses of proteins present in a known organism, organ, tissue, or cell-type. There are a number of algorithms to identify open reading frames (ORF) and convert nucleotide sequences into protein sequence and molecular weight information. Several publicly accessible biomarker/genome/proteome databases are available, including, GenBank (National Center for Biotechnology Information) and SwissPROT/TrEMBL database, which is part of the Uniprot database. Information contained in the databases can include, e.g., gene name, protein name, E.C. number, category of function, Swiss-Prot accession code, sequence code for Genbank, Kohara phage location, genetic map location, direction of transcription on the chromosome, predicted molecular weight and isoelectric point from DNA sequence, etc.

In matching a molecular mass calculated from a mass spectrometer to a molecular mass predicted from a database, such as a genomic or expressed gene database, post-translation processing may have to be considered. There are various processing events which modify protein structure in a cell, including, proteolytic processing, removal of N-terminal methionine (see, e.g., Demirev et al., *Anal. Chem.* 2001, 73 4666-4573), acetylation, methylation, glycosylation, etc. However, as compared with eukaryotic cells, most microorganisms in accordance with example embodiments of the present invention have little, if any, post-translational processing of the biomarkers.

The mass shifts in the spectra for an unknown organism, when grown in control versus isotopically-labeled media, can be directly calculated from the respective biomarker protein amino acid sequences, identified in the genomic/proteomic database.

The ratio of intensities of isotopically-shifted mass peaks for the same organism grown at different drug concentrations (and/or different drugs) under otherwise identical conditions, can be a semi-quantitative measure of the microorganism's drug resistance. In some embodiments, an appropriate internal standard (a labeled/unlabeled molecule with mass not contained in the organism MS signature) can be added in a known concentration to the sample after growth, to facilitate quantitative determination of specific biomarker molecules by quantitative MS.

These algorithmic options of FIG. 4 can be used individually, or in combination to increase the confidence in the conclusion.

Each of the algorithmic options of FIG. 4 yields a list of predicted masses or mass ranges for which new peaks are expected to be observed in a spectrum of a drug-resistant microorganism grown in an isotopically-labeled medium in the presence of the drug. This spectrum will yield a list of biomarker peaks, each with a calculated signal-to-noise ratio (SNR), and assigned mass/charge ratio.

Detection of biomarker masses (from both control and isotopic spectra) can be accomplished using any number of possible threshold values for determining signal to noise in a spectrum. For instance, in one embodiment biomarkers would not be determined unless that have an intensity (a.u) level of at least 500. Further, the intensity could be in a range from 500 to 4000. Other intensity thresholds or ranges could be used with the present embodiments.

Probabilistic Algorithm

After comparison of biomarker mass shifts 436 (see FIG. 4) and threshold significance of observations 438 (see FIG. 4) have been determined, matching of mass shifts to respective biomarkers can be accomplished.

Figure 5:
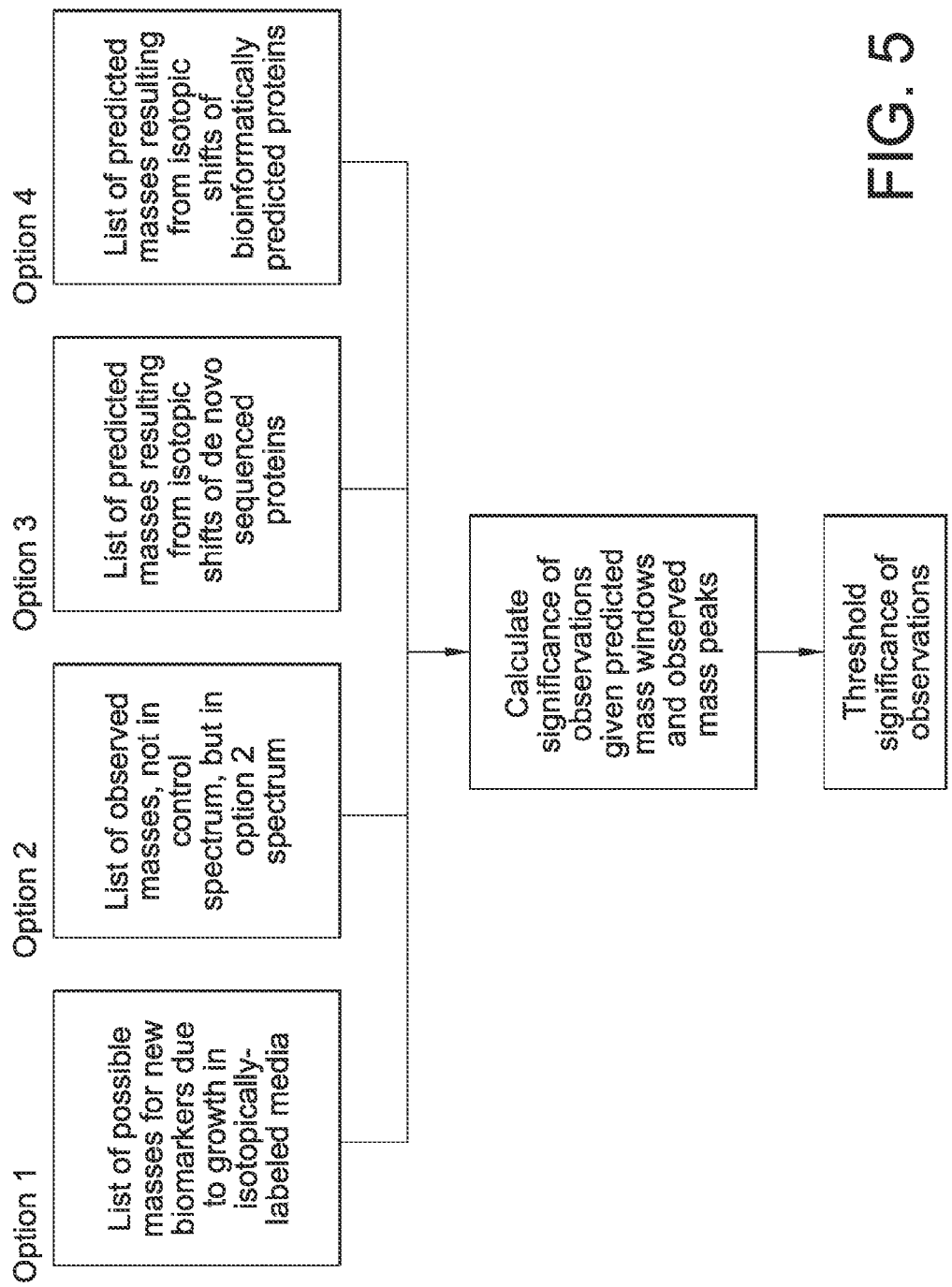
FIG. 5 shows a schematic diagram of algorithmic module processing options that can be employed by the methods and systems according to example embodiments of the invention.

In some embodiments of the invention, the correspondence of the predicted masses and mass ranges with the observed experimental peaks can then be used to calculate a measure of the degree of match, for example, a statistical significance of the observations or probabilistic measure (FIG. 5).

In some embodiments, the invention utilizes a probabilistic algorithm for calculating the measure of the degree of match between a predicted and an observed value. In some embodiments, a signal-to-noise ratio (SNR) threshold is applied to selected high signal peaks. The statistical significance of the observations can be calculated as the probability of observing peaks due to an unknown process and misinterpreting them as the predicted peaks. The number of new observed peaks that match predicted masses by falling within an instrument precision/mass assignment error window around the predicted masses can be counted. For example, a mass window ($\delta m$) can be set to define a mass range around the predicted peaks in which matches of observed peaks will be scored as hits. The mass window for a particular query can be set based on various criteria. Some considerations relate to the accuracy of the instrument and purity of the isotopically-labeled media. In addition, if an algorithm is used which predicts a mass shift based on an average elemental composition in a protein (see option 1, above), a mass range in some embodiments will encompass possible proteins that have only amino acids with the least number of C-atoms per mass and proteins with the highest number per mass, for example, for the case of $^{13}C$-labeling. Other considerations, include, post-translational processing. The accuracy of the instrument can be determined routinely, e.g., using known standards and calibrating the instrument using an external and internal standard.

In some embodiments, $\delta m$ is 1.0 Da (i.e., ±0.5 Da around the predicted peak), 2.0 Da, 2.5 Da, 3.0 Da, 4.0 Da, 5.0 Da, 6.0 Da, 7.0 Da, 8.0 Da, 9.0 Da or 10.0 Da. In some embodiments, $\delta m$ is larger.

In some embodiments, the algorithm for calculating the measure of the degree of match between a predicted and an observed value is $p_{match}$, an accidental match probability, which is a function of the number of predicted peaks, n, the expected mass error when observing these peaks, $\delta m$, and the number of new peaks observed in the spectrum, k, and the number of observed matches, K, and is shown below.

$$P_{match} \equiv 1 - P(0) \equiv 1 - e^{-p\Delta m}$$

In the above equation, $p = n/(m_{max} - m_{min})$ is the density of proteins in the proteome in the mass range $[m_{min}, m_{max}]$. Taking into account the form of $p_{match}$ and the number of ways that k matches can be selected from K peaks yields:

$$P_K(k) = \frac{K!}{(K-k)!k!} e^{-(K-k)n/n^*} (1 - e^{-n/n^*})^k$$

wherein $$n^* \equiv \frac{m_{max} - m_{min}}{\delta m}.$$

The above derived distribution of false matches can be used to test H0 (the null hypothesis that the unknown and the known proteomes are not the same by calculating the probability that the score exceeds the observed score, $k_{obs}$ $$\alpha = P(k \geq k_{obs} | H_0) = \sum_{k=k_c}^{K} P_K(k)$$

The above algorithm is described in Pineda et al., *Anal. Chem.* 2000, 72, 3739-3744, herein incorporated by reference. This algorithm or slight variations for calculating the measure of the degree of match can be found, for example in Demirev et al., *Analytical Chemistry* 77 (2005) 7455-7461 and Eriksson, *J. Anal. Chem.* 72, 999-1005 (2000), wherein incorporated by reference herein.

In some embodiments, n, the number of predicted peaks is between 5 and 150. In some embodiments n is between about 10 and 100, between about 10 and 75, between about 10 and 50, or between about 15-30.

In some embodiments, $m_{max}$ is about 150 kDa, about 130 kDa, about 120 kDa, about 110 kDa, about 100 kDa, about 90 kDa, about 80 kDa, about 70 kDa, about 60 kDa, about 50 kDa, about 40 kDa or about 30 kDa. In some embodiments, $m_{min}$ is about 5 kDa, about 8 kDa, about 10 kDa, about 15 kDa, about 20 kDa, about 25 kDa, about 30 kDa, about 35 kDa, about 40 kDa, about 45 kDa, about 50 kDa. In some embodiments $m_{min}$ is between 5-20 kDa and $m_{max}$ is between 40-100 kDa. In some embodiments, $m_{min}$ is about 10-15 kDa and $m_{max}$ is about 35-50 kDa. In some embodiments, $m_{min}$ is about 10 kDa and $m_{max}$ is about 50 kDa.

In some embodiments, the probability of an accidental match of predicted and observed peaks, $\alpha$ is between about 0.05 and $1.0 \times 10^{-30}$ or less. In some embodiments, $\alpha$ is less than 0.05, 0.01, 0.001, 0.0001, 0.00001, 0.000001, 0.0000001, 0.00000001, 0.000000001 or 0.0000000001. In some embodiments a is less than $1 \times 10^{-11}$, $1 \times 10^{-12}$, $1 \times 10^{-13}$, $1 \times 10^{-14}$, $1 \times 10^{-15}$, $1 \times 10^{-16}$, $1 \times 10^{-17}$, $1 \times 10^{-18}$, $1 \times 10^{-19}$, $1 \times 10^{-20}$, $1 \times 10^{-21}$, $1 \times 10^{-22}$, $1 \times 10^{-23}$, $1 \times 10^{-24}$, $1 \times 10^{-25}$, $1 \times 10^{-26}$, $1 \times 10^{-27}$, $1 \times 10^{-28}$, $1 \times 10^{-29}$, or $1 \times 10^{-30}$.

Selecting the appropriate SNR threshold for including observed peaks in the measure of the degree of match will be arbitrary. In addition, the list of predicted biomarker mass shifts may be extensive. Not every mass shift might be expected to be observed with the same probability due to differences in protein expression level during a particular microorganism life stage, for example. In many cases it is possible to rank the list of predicted observed mass shifts, for example by the probability or likelihood of observation or by other heuristic importance. If this is the case, one reasoned approach to selecting both the SNR threshold and the number of predicted peaks, n, is to maximize $p_{match}$, over all possible combinations of SNR thresholds and probability of peak observation thresholds. This calculation can be made very efficient by recording for each predicted mass, starting with the most probable predicted mass, the rank of the unused peak with highest SNR that matches the predicted mass. Then for each predicted mass, knowing the SNR threshold required to observe this and all other matches to predicted masses of higher probability, the significance of observing that match with all other matches of higher probability than that match can be calculated (see Example 2, below). The minimum significance, $p_{match}$, calculated over all predicted masses is the representative significance for the observed matches.

In some embodiments, the matches between predicted masses for the algorithmic options shown in FIG. 4 (and discussed above) and observed peaks in experimental sample can be fused before or after the significance or probabilistic measure of the matches are calculated. An example of fusing before the significance is calculated, the predicted peak lists can be merged with only slight changes to the algorithm required. An example of fusing after the significance is calculated is to assume that the significance of matching for each list of predicted masses is independent, and the joint significance is simply the product of the individual significances.

Application of the teachings of example embodiments of the present invention to a specific problem is within the capabilities of one having ordinary skill in the art in light of the teaching contained herein. Examples of the systems and methods of the invention appear in the following non-limiting Examples.

EXAMPLES

Example 1

Correlation between experimentally-observed and predicted mass shifts, Δm, for selected biomarkers.

Test organism cultures and sample preparation for mass spectrometry (MS) analysis:

All chemicals were obtained from Sigma Chemical Co. (St. Louis, Mo., USA) and were used without further purification. Organisms (*E. coli*) were isolated on tryptic soy agar and one colony from a plate was inoculated into three separate flasks and incubated for six hours at 37° C. Two flasks contained a standard growth medium with natural $^{13}C$ isotopic abundance (Bioexpress 1000 growth medium: CGM-1000-U-S (unlabeled, 10× concentrate)—Cambridge Isotope Laboratories, Inc. Andover, Mass.), while the third flask contained a $^{13}C$ isotopically-enriched growth medium (Bioexpress 1000 growth medium: CGM-1000-C-S ($^{13}C$—98%, 10× concentrate)—Cambridge Isotope Laboratories, Inc. Andover, Mass.). Streptomycin (drug) was introduced into one of the natural isotopic abundance cultures (control sample 132 in FIG. 3A) and to the culture containing isotopically-enriched media (drug trial 122, FIG. 3A) to determine organism susceptibility. No streptomycin was added to the No Drug sample 134 (FIG. 3A). One milliliter was removed from each flask and the culture medium was washed several times in deionized H$_2$O. Pelleted bacteria were resuspended in deionized water corresponding to roughly $10^6$ cells per mL and 0.5 μL of the intact cell suspension was deposited into an individual sample well of a commercial (Bruker Daltonics) stainless steel slide. The matrix, alpha-cyano-4-hydroxycinnamic acid (CHCA), was dissolved in 1:1 acetonitrile/water (v/v). An aliquot of the CHCA matrix solution (0.5 μL) was added to each sample well containing the bacteria and the samples were left to air dry.

MS Analysis

Positive and negative ion mass spectra were obtained in linear mode using a Bruker MicroFLEX MALDI-TOF instrument (Bruker Daltonics, Billerica, Mass., USA) at 20 kV nominal accelerating voltage. Pulsed ion (delayed) extraction was optimized for ion focusing and transmission at m/z 8000. The 337 nm UV N2 laser ('VSL-337ND'; Laser Science Inc., MA, USA), focused into an elliptical spot had the following typical parameters: 200 mcJ average energy/pulse prior to attenuation (typically 30%), and 4 ns pulse duration. Commercial protein samples (ubiquitin, bovine insulin, were used for external instrument calibration. The estimated mass accuracy and mass resolving power at 8 kDa are 3 Da and >400 (FWHM), respectively. For each spectrum, the laser beam was rasterred across the entire sample well and typically 600 individual traces from single laser shots were accumulated. The spectra were averaged and initially processed using the software provided with the instrument.

FIGS. 3A and 3B show the results of MALDI TOF MS signatures of intact microorganisms to determine drug resistance. FIG. 3A shows the results of *E. coli* grown in a $^{13}C$ enriched medium with no drug (similar to no drug trial 134 and no drug trial spectrum 134'). FIG. 3B shows the results of *E. coli* grown in a control medium with no drug. Δm shows the mass shifts for each associated m/z ratio in each of the spectra. The mass shift observed between respective *E. coli* K12 biomarker protein peaks is proportional to the number of C-atoms. Further, the mass shift, Δm is seen to increase with increasing biomarker mass. This is one reason to analyze the results and correlate peaks using algorithmic analysis. Table 1 compares the experimentally-observed and predicted mass shifts for selected biomarkers of *E. coli* K12 grown both in control media and $^{13}C$ isotopically enriched growth media.

The prediction is based on a statistical amino acid "averagine" with elemental composition: $C_{4.9384}H_{7.7583}N_{1.3577}O_{1.4773}S_{0.0417}$ ($M_{ave}$: 111.1254 Da). The differences between observed and predicted mass shifts are due to differences between actual and predicted number of C-atoms in a molecule. The ratios of $^{13}C$ to $^{12}C$ are 0.01 and 46, for natural abundance and isotopically-labeled media, respectively.

TABLE 1

| Mass of biomarker [Da] (natural isotope abundance) | Observed mass shift Δm [Da] | Predicted number of C-atoms per biomarker molecule | Predicted mass shift Δm [Da] |
| --- | --- | --- | --- |
| 4366 | 178 | 193 | 188 |
| 5095 | 208 | 226 | 220 |
| 5751 | 221 | 256 | 249 |
| 7265 | 314 | 323 | 314 |
| 8310 | 348 | 369 | 359 |
| 9038 | 385 | 402 | 391 |

The algorithm used in the above example corresponds to Option 1 above. The example is helpful in determining whether a known microorganism is susceptible to a drug or rather is drug-resistant.

Example 2

Comparison of Observed and Predicted Masses

An exemplary study is conducted in accordance with the systems and methods of the invention. The following masses are predicted according to algorithmic analysis: (ranked by probability of observation): 1. 5000-5100; 2. 4000-4100; 3. 7000-7100; 4. 6000-6100; 5. 3500-3600.

The following masses are observed in the experimental sample of the microorganism grown in isotopically-labeled media with the drug (ranked by SNR): 1. 4070; 2. 5020; 3. 8000; 4. 3550; 5. 7500; 6. 3550.

TABLE 2

| Predicted mass rank, n | Predicted mass range | Observed peak mass | Observed peak rank | Probability match parameters |
|---|---|---|---|---|
| 1 | 5000-5100 | 5020 | 2 | n = 1, K = 2, k = 1, $\delta m$ = 100 |
| 2 | 4000-4100 | 4070 | 1 | n = 2, K = 2, k = 2, $\delta m$ = 100 |
| 3 | 7000-7100 | — | — | |
| 4 | 6000-6100 | — | — | |
| 5 | 3500-3600 | 3550 | 4 | n = 5, K = 4, k = 3, $\delta m$ = 100 |
| 6 | | | | |

While the present teachings are described in conjunction with various embodiments, it is not intended that the present teachings be limited to such embodiments. On the contrary, the present teachings encompass various alternatives, modifications, and equivalents, as will be appreciated by those of skill in the art.

What is claimed is:

1. A system for determining the resistance of a microorganism to a drug, comprising:
   (a) a sample growth and processing module for isotopic labeling and processing of a sample;
   (b) a mass spectrometry acquisition module down-stream from the sample growth and processing module for detecting and analyzing the isotopically-labeled and processed sample; and
   (c) an algorithmic module down-stream from the mass spectrometry acquisition module for processing the results from (b) and determining whether the microorganism is drug-resistant, wherein
   the sample growth and processing module comprises an isotopically-labeled growth medium and a control medium, and the sample growth and processing module incubates the microorganism in each of the isotopically-labeled growth medium and the control growth medium, the isotopically-labeled growth medium comprises at least one drug and an isotopic label such that the microorganism incorporates the isotopic label into one or more biomarker molecules of the microorganism during growth in the isotopically-labeled growth medium, and the control growth medium lacks the drug and the isotopic label such that the one or more biomarker molecules of the microorganism remain unlabeled during growth in the control growth medium,
   the mass spectrometry acquisition module receives a sample comprising the biomarker molecules of the isotopically-labeled growth medium and a sample comprising the biomarker molecules of the control growth medium to a mass spectrometry system and produces ion mass fragments of the biomarker molecules of each of the isotopically-labeled growth medium and the control growth medium, and
   the algorithmic module:
      analyzes the ion mass fragments of tile biomarker molecules of the control growth medium and uses said analysis to determine a predicted mass for the one or more biomarker molecules of the isotopically-labeled growth medium using an algorithm that determines a predicted mass based on the incorporation of the isotopic label into the one or more biomarker molecules of the control growth medium,
      compares the predicted mass with an observed mass of the one or more biomarker molecules of the microorganism growing in the isotopically-labeled medium with a drug thereof using an algorithm based on a probability that the biomarker molecules in the two media match can be determined, thereby indicating whether growth of the microorganism has occurred in the isotopically-labeled medium when the biomarkers have a high probability of matching, and
      determines the microorganism to be resistant to the drug if the biomarkers have a high probability of matching.

2. The system of claim 1, wherein the sample growth and processing module comprises at least two isotopically-labeled growth media.

3. The system of claim 1, wherein the sample growth and processing module comprises at least two control growth media.

4. The system of claim 1, where the sample growth and processing module includes at least one chromatography technique selected from the group consisting of HPLC, CE, and 2D-gel electrophoresis.

5. The system of claim 1, wherein the mass spectrometry acquisition module comprises single MS system.

6. The system of claim 1, wherein the mass spectrometry acquisition module comprises an MS/MS system.

7. The system of claim 1, wherein the mass spectrometry acquisition module comprises a mass spectrometry system selected from the group consisting of TOF, TOF/TOF, AP-MALDI, ion trap, quadrupole, triple quadrupole, FTICR, Orbitrap, electric and magnetic mass analyzers, ion mobility analyzers, and/or a combination thereof.

8. The system of claim 1, wherein the algorithmic module comprises at least one biomarker composition database.

9. The system of claim 1, wherein the algorithmic module comprises at least one genome or proteome database.

* * * * *